(12) United States Patent
Risse

(10) Patent No.: US 6,595,774 B1
(45) Date of Patent: Jul. 22, 2003

(54) ORTHODONTIC ARCH

(76) Inventor: Georg Risse, Bogenstrasse 15/16, D-48143, Munster (DE)

( * ) Notice: Subject to any disclaimer, the term of this patent is extended or adjusted under 35 U.S.C. 154(b) by 0 days.

(21) Appl. No.: 09/868,759

(22) PCT Filed: Dec. 22, 1999

(86) PCT No.: PCT/EP99/10285

§ 371 (c)(1),
(2), (4) Date: Jun. 21, 2001

(87) PCT Pub. No.: WO00/36988

PCT Pub. Date: Jun. 29, 2000

(30) Foreign Application Priority Data

Dec. 22, 1998 (DE) .......................... 198 59 503

(51) Int. Cl.[7] .................................. A61C 3/00
(52) U.S. Cl. ................................ 433/21; 433/18
(58) Field of Search .................. 433/18, 20, 21, 433/22

(56) References Cited

U.S. PATENT DOCUMENTS

| | | | |
|---|---|---|---|
| 3,178,822 A | 4/1965 | Fogel et al. ................ 32/14 |
| 3,600,808 A | * 8/1971 | Reeve ....................... 433/21 |
| 4,197,643 A | 4/1980 | Burstone et al. ............ 433/20 |
| 4,268,250 A | 5/1981 | Reeve ....................... 433/21 |
| 4,412,819 A | 11/1983 | Cannon ...................... 433/20 |
| 4,975,052 A | * 12/1990 | Spencer et al. ............. 433/21 |
| 5,092,768 A | 3/1992 | Korn ......................... 433/18 |
| 5,131,843 A | 7/1992 | Hilgers et al. .............. 433/20 |
| 5,246,366 A | * 9/1993 | Tracey ....................... 433/21 |
| 5,984,675 A | * 11/1999 | White ........................ 433/21 |

FOREIGN PATENT DOCUMENTS

DE          35 42 714 C2          12/1985

* cited by examiner

*Primary Examiner*—Cary E. O'Connor
(74) *Attorney, Agent, or Firm*—Westman, Champlin & Kelly, P.A.

(57) ABSTRACT

The present invention relates to an orthodontic arch (12) comprising at least one special loop (22) in the form of a spring hook. Said spring hook makes it possible to effect intrusion and corporal retraction of the front teeth, especially in the upper jaw, in a faster, more gentle and better controlled manner in comparison with conventional arches and methods. By additionally attaching rubber bands, springs or ligatures (24), all disadvantages of conventional constructions can be eliminated or minimized by means of an adjustable lever action effect due to the fact that the inventive arch-spring construction enables dynamic undulating movement of the front teeth adapted to biological processes during an activation procedure as opposed to conventional rigid mechanisms. Especially medical or biological requirements and aspects are fulfilled by the inventive arch. The inventive arch enables faster movement and greatly reduces damage and pain. In addition, the costs are lowered considerable by reducing the number of arches and by saving time.

29 Claims, 8 Drawing Sheets

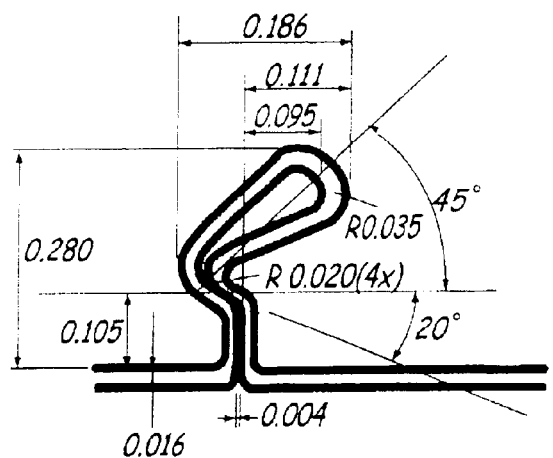
Fig. 15
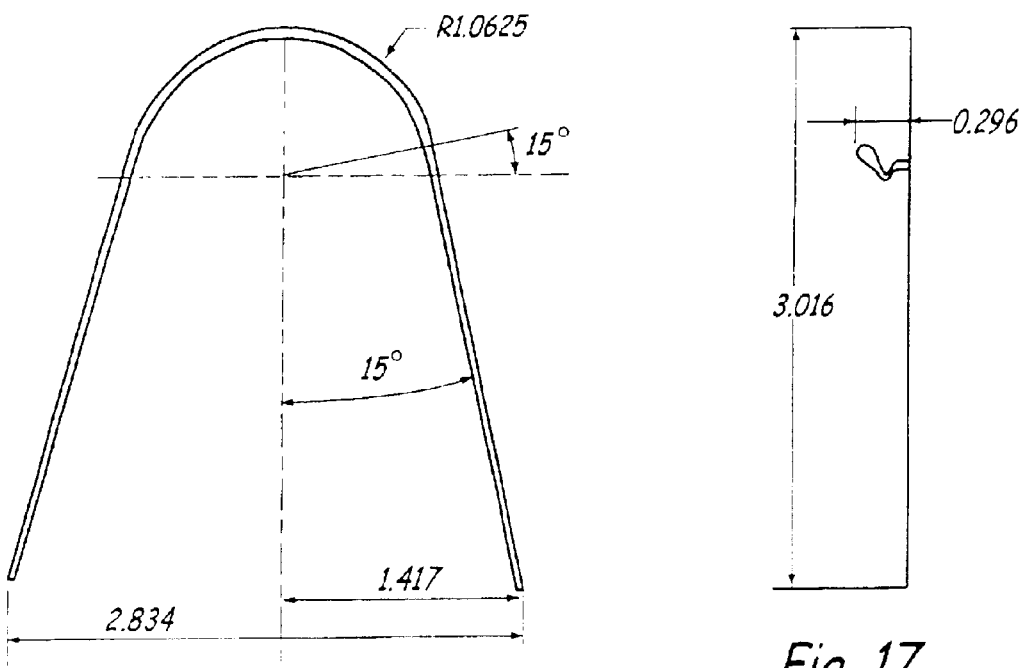
Fig. 16
Fig. 17

ORTHODONTIC ARCH

The present invention relates to an orthodontic arch for making it in particular possible to effect intrusion and corporal retraction of front teeth, especially in the upper jaw, in a faster, more gentle and better controlled manner as compared to conventional arches and methods.

Orthodontics is a treatment method in dental orthopedics in which rigid appliances are used. Brackets/tapes having specific slots are applied to the teeth in the upper and lower jaws. In the Edgewise technique, preferably rectangular slots having specific dimensions and angles are provided for this purpose. So-called arches, preferably made of square wires, are inserted in the slots; along these wires or by means of these wires a torsion or angulation imparts forces to the teeth in order to bring them into a different position. A specific and difficult problem in dental orthopedics regularly occurs in case of a so-called "deep bite" in which the upper front teeth bite vertically considerably over the lower front teeth. For a correction, the upper front teeth have to be intruded vertically, i.e. they have to be pushed again back into the jaw.

A mere intrusion, however, is rarely necessary; rather, in most cases also especially the roots of the front teeth have to be moved in the distal direction, i.e. towards the back. For this purpose, the front teeth are preferably tilted by a distortion of the square arch, wherein the point of rotation is located in the slot. This is also called torque. If the square arch is distorted much, the torque normally causes an extrusion of the front, i.e. exactly the opposite of the desired movement.

An even larger degree of difficulty is caused if extraction gaps, e.g. of the teeth Nos. 4 and 5 have to be closed, wherein at the same time front teeth have to be intruded and the roots of the front teeth have to be moved corporally in the distal direction, since an even stronger torque is required for this purpose, which means at the same time an increased extrusion.

It is pointed out in general that the individual teeth in the upper and lower jaws are enumerated from the center (mesial) towards the back (distal), wherein it is in each case started with "1". The arch according to the present invention, which is described in the following, is preferably but not necessarily realized such that it can be used for a similar, symmetrical treatment of both sides of the respective jaw.

Normally, first the canine teeth are moved in the distal direction along a continuous arch or along partial arches, thereby using loops, if, e.g., the teeth Nos. 4 or 5 are extracted, wherein the rear teeth (e.g., the teeth Nos. 5 and/or 6) are used as an anchorage. If the teeth No. 3 are in the respective positions of the original teeth No. 4, a relatively large gap has been generated in the distal direction of the teeth No. 2. The front, i.e. the teeth Nos. 1 and 2, are then commonly drawn backwards in one block. Thus, the above-mentioned vertical and angulation problems are caused in connection with anchorage problems from distal to mesial. In concrete terms, the rear anchorage teeth move too much towards the front.

This movement of the four front teeth, sometimes also of the six front teeth, in the distal direction is partially carried out by means of continuous arches to both sides of which one vertical hook is soldered. At this vertical hooks additional forces are applied by means of rubber bands which are anchored for the second time at the teeth No. 6 in the upper jaw or in the counter jaw. An example of such a conventional arrangement is shown in FIG. 1. This arrangement to which hooks are soldered or screwed is a very rigid system which is a biological and causes considerable damage. Moreover, extreme anchorage losses are caused and it is difficult to estimate the ideally applicable forces and/or the forces being practically actually applied.

In a second conventional form of distalization of the front teeth, a square arch having vertical loops (so-called bulloops) in the distal direction of the teeth Nos. 2 or 3 is used. Such an arch is shown, for example, in DE-C-35 24 714. These loops act as a spring and are first closed and then opened by activation in order to cause a resilient tensile force. The "activation" preferably takes place by fixing the arch in the distal direction at the respective anchor tooth, e.g. the teeth Nos. 6 or 7. The tensile force applied by the resiliency of the spring takes the front teeth with it, as shown, for example, in FIG. 2. This arrangement and method is biologically better tolerable and more elastic; however, due to the loops there is the disadvantages that the movement in the distal direction goes along with a very strong tilting movement of the crowns in the distal direction and that due to the strong torque which is required also an extrusion of the upper front teeth has to be expected, i.e. altogether a strong tilting of the crowns downwards in the distal direction. As mentioned, these movements have negative effects and must be counteracted by other arches. This means that additional time is necessary and thus additional costs arise.

The square orthodontic arches known from the prior art, e.g. for treating the above-mentioned diseases, are all disadvantageous in that the rigid system tends to cause an overactivation and then the front teeth have to be moved in a position which is unfavorable as regards anchorage, comparable to a plough through the ground. The biological tissue is thus not offered the necessary rest phases.

U.S. Pat. No. 5,131,843 describes an orthodontic arch for imparting forces to teeth. The arch is essentially U-shaped and has a central front portion and a pair of rear portions extending at both sides of the front portion. Moreover, the arch comprises a pair of T-loop elements, wherein one of the T-loop elements is provided at any side of the mesial center line. Each of the T-loop elements has a pair of legs which extend essentially vertically and are adjacent to each other and which form an essentially closed loop at its upper end. The upper cross-loop of the T-shape extends essentially parallel to the arch.

U.S. Pat. No. 5,092,768 relates to a removable appliance for distalizing the lips or for keeping the lips away from the teeth. In order to provide an as large as possible rest area for the lips, loops are bent-in in a wire. The wire is fixed at the two molars.

U.S. Pat. No. 4,412,819 describes an orthodontic arch with front and rear portions having a different elasticity and strength, wherein a central portion made of a relatively resilient wire and rear portions made of a different and harder wire are formed. Moreover, different cross-sectional shapes can be realized in the portions.

It is the object of the present invention to provide an improved orthodontic arch which is particularly suitable for regulating the above-described phenomena in a better way.

Thus, a system should be developed which is biological, flexible, fast and better controllable, widely avoids damages as well as exhibits minimum anchorage losses.

For achieving this object, the invention starts out from the basic idea of achieving the desired improved intrusion and torque movements by means of a novel lever system, so that minimum forces have to be applied and the system is flexible. For this purpose, the arch comprises a spring hook which preferably extends obliquely to the arch direction.

It is an essential aspect of the present invention that a favorable mechanical force application (lever and at the same time spring) and not only directly action-reaction is striven for, this interaction taking into account the biological aspects more strongly. In medicine in general and thus also in dental orthopedics, the biological factors such as, e.g., blood supply play an important role in order to effect the desired change as biologically, painlessly and quickly as possible. If the blood supply is compressed, there is no movement since no transformation of the bone is possible due to the lack of blood. This means that in the biological, living tissue the proportion between applied force and achieved movement speed is practically reversed since the blood supply is reduced as the force increases. In the biological field the biological relationships must thus be taken into consideration when physical laws are applied.

The arch according to the present invention can extend both along all teeth of the respective jaw and only along parts thereof, in particular in the front. If the arch is provided only in the area of the front teeth, the anchorage is preferably provided in the area of the canine teeth.

In the following the invention is described on the basis of preferred embodiments by means of drawings in which FIG. 1 is a prior art system with a continuous arch with vertically attached hooks;

FIG. 15 is a representation of the spring hook of FIG. 14 with dimensioning; and FIGS. 16–17 show the preferred position of the spring hooks at the arch according to the present invention including dimensioning.

Figure 1:
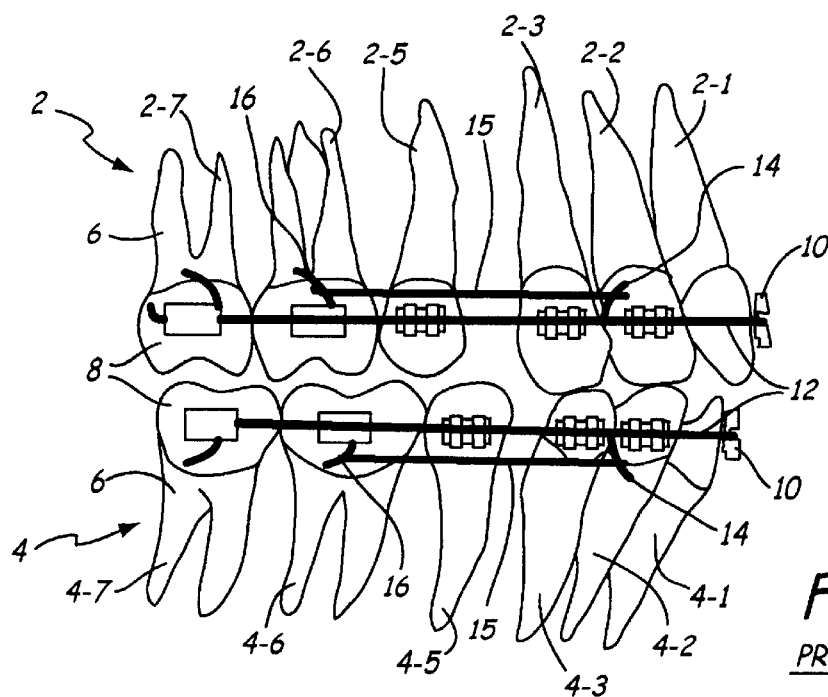
Figure 2:
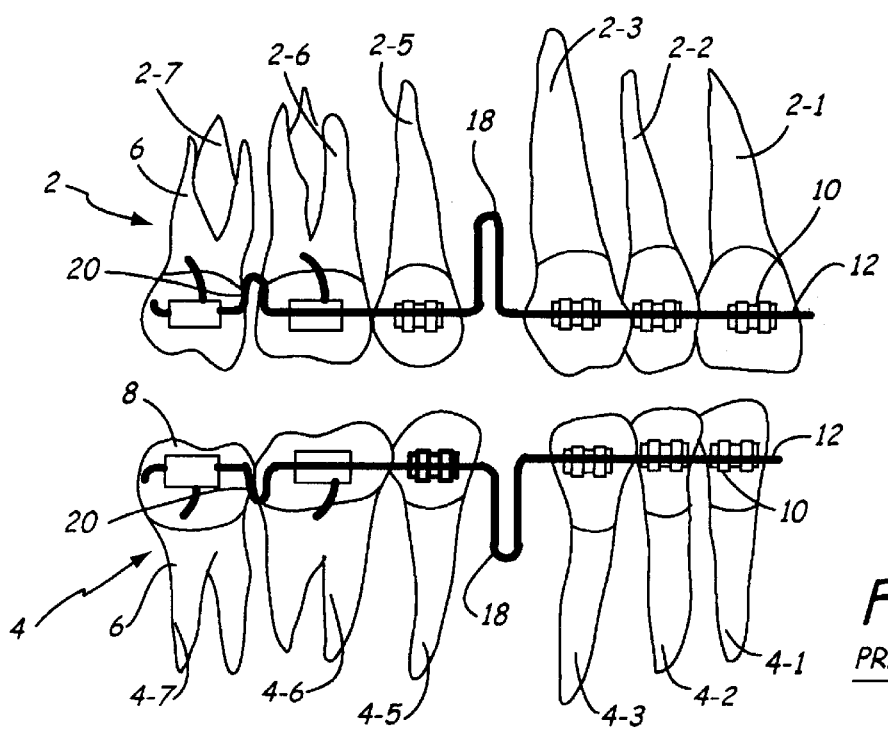
FIG. 2 is a prior art system with a continuous arch and bulloops.
Figure 3:
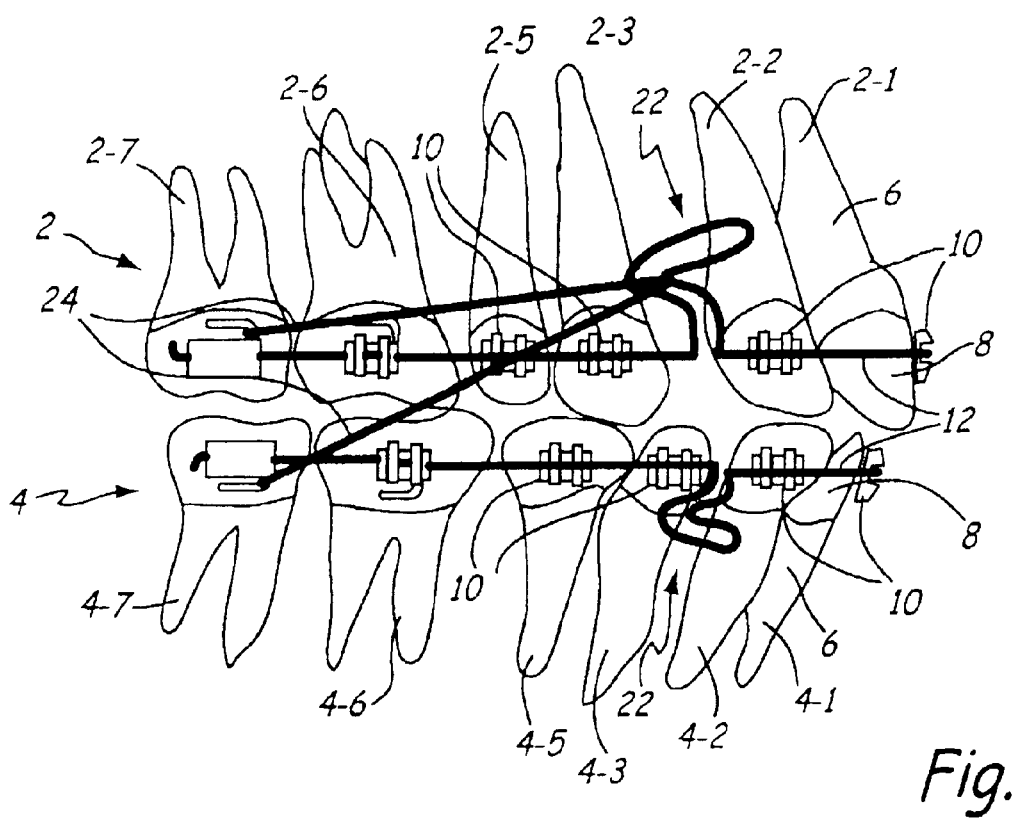
FIG. 3 is an embodiment of the system of the present invention with a square arch and rubber bands.

The arrangements of FIGS. 1 to 3 show teeth 2-i in the upper jaw 2 and teeth 4-i in the lower jaw 4 of a patient. The extension "i" means i-th tooth in the upper or lower jaw according to the common definition based on the mesial line. Each of the teeth 2-i and 4-i has a root area 6 located in the jaw, as well as a crown 8 protruding therefrom.

To each of the crowns 8 of the teeth 2-i and 4-i preferably one bracket 10 with a slot extending in the mesialdistal direction, i.e. sagital direction (shown only schematically) is attached. As already explained above, the slots are shaped such that a continuous arch 12 or several individual arches (not shown) are guided through them in order to introduce together forces into the respective teeth 2-i and/or 4-i.

As already described above, a conventional kind of front tooth retraction is given in that a vertical hook 14 is provided at the continuous arch 12. Rubber bands 15 are hooked in the vertical hook 14, said rubber bands 15 having their second anchorage 16, e.g., at the teeth Nos. 6, 2-6 in the upper jaw and/or 4-6 in the counter jaw.

Figure 6:
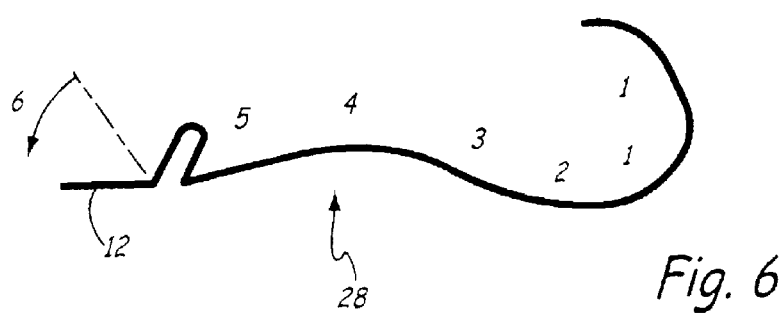
FIG. 6 is a conventional straight, non-bent arch in which a front torque and/or a strong angulation of the wire are bent in at the tooth No. 6.

For displacing the front teeth 2-1, 2-2 and optionally 2-3 in the upper jaw and the front teeth 4-1, 4-2 and optionally 4-3 in the lower jaw (for symmetrical reasons it is preferred on both sides), the entire arch 12 must be displaced through all brackets 10 in the side area. This means that the arch 12 must be displaced through the brackets 10 located on the teeth 2-5, 2-6 and 2-7 as well as 4-5, 4-6 and 4-7. In order to achieve this, strong forces are required, in particular for overcoming the strong frictional forces and the "plough angulation" of the front teeth (point of rotation in the slot=corporal movement). The strong forces in turn cause a considerable loosening and damage at the tooth tips (in up to 65% of the cases) of especially the anchoring teeth and the front teeth as well as strong pain and slower movements due to compression of the blood supply, which leads to strong anchoring losses. This is synonymous with an undesired tilting of the crowns of the anchorage teeth in the mesial direction. As shown in FIG. 6, an elastic torque of the arch in the area of the teeth Nos. 4 and 5 towards the top is thus increased, which is also additionally caused and increased by a necessary active torque in the front; this additionally causes a strong friction. This could be reduced if the hooking appliance 14 is arranged at a somewhat higher position; however, in the conventional rigid system this would at the same time increase friction and the anchorage problems due to the lever mechanism, and thus hinder the desired passing-through of the arch since friction is caused by the lever.

The appliance shown in FIG. 2 for a distalization of the front teeth 2-1, 2-2, 2-3 and/or 4-1, 4-2 and 4-3 is based on the appliance described above. However, instead of the hooks 14, the counter attachment positions 16 and the rubber bands 15, so-called bulloops 18 are arranged in the distal direction of the teeth Nos. 2 or 3, i.e. 2-2, 2-3 and/or 4-2, 4-3. A bulloop 18 is a loop which is provided essentially vertically with respect to the mesial-distal direction of the arch 12. The loops represent a spring which, when trying to close itself, takes the front teeth with it in the distal direction. The bulloops 18 or the springs are mounted in the closed state and then activated in order to impart their forces. For the purpose of activation, a so-called tieback loop 20, which activates the bulloops 18 when being provided on the teeth Nos. 7, i.e. 2-7 or 4-7, is provided between the teeth Nos. 6 and 7, i.e. 2-6 and 2-7 or 4-6 and 4-7. This appliance or this method have the considerable disadvantage that the movement in the distal direction goes along with a strong tilting movement of the crowns 8 of the upper front teeth downwards in the distal direction and, due to the necessary strong torque, also an extrusion of the front teeth is caused. As already explained above, these movements must be regulated later by means of different arches.

In the appliance according to the present invention as exemplarily shown in FIG. 3, the disadvantages known from the prior art are avoided or minimized. This is particularly due to an improved control of the intrusion and torque movements which is achieved by a novel spring and lever system.

The invention is based on the idea of providing the arch 12 with at least one special "spring hook" 22, which can also be called a loop or spring 22, preferably in the front. In contrast to known bulloops, the spring hook 22 is bent or forms an angle and has at least one part which does not extend vertically and/or parallel to the arch 12. The spring hook 22 is preferably bent several times, e.g. bent two times. Thus, the spring hook 22 can impart force components having different directions and strengths to the teeth and can act in different partial areas as a pressure and/or tension spring. The spring hook 22 is preferably attached in the closed state. A slight drawing-through of the rear part of the arch 12 and subsequent attachment to the anchor tooth leads to the opening of the spring hook 22 and its activation. Due to its geometric construction and position (cf., for example, FIGS. 4, 5 and 7 to 9), the spring hook 22 imparts an intrusion force to the front teeth and thus causes a counter force to the extruded components in the front. The spring hook 22 is preferably located in the area at the distal side of the teeth Nos. 2 or 3 and at the mesial side of the teeth Nos. 4 or 5. This approximately corresponds, e.g., in an area extending from the mesial line in the distal direction about 10% to 50% of the length of the arch 12 from the mesial line or center of the arch to the distal end (10% to 50% of the length of half of the arch). The presently preferred position of the spring hook 22 is shown in more detail in FIGS. 16 and 17. In accordance therewith, with a radius of the arch of about 27 mm (1.0625 Inch) the spring hooks 22 are located in the area of the front teeth about 75° away from the mesial line or center of the arch.

As an alternative, for activating the spring hook 22 a tieback loop 20 with a ligature can also be provided and fixed to the respective anchor tooth.

For providing an active torque for the distalization of the roots 6 in the area of the front teeth, the arch 12 is, for example, distorted in the front. Due to this bend, the torque will also simultaneously draw the crowns 8 of the front teeth in the distal direction due to a center of rotation which adapts itself depending on the course of movements, as compared to conventional techniques. Thus, since the spring hook 22 is shaped in accordance with the present invention, the point of rotation can move from the slot to the tip of the root or vice versa, depending on the treatment situation. During a course of activation or movements, the arch construction according to the present invention, which can also be understood as a spring construction, first more or less yields different moments, depending on the thickness of the wire and the torsion. This is more favorable in a biological and vectorial sense for moving the upper front teeth upwards in the distal direction. In this connection, it must be taken into consideration that during its sagital activation the construction according to the invention at the same time causes a vertical intrusion component. Due to the lighter forces and the center of rotation which adapts itself, the blood supply is maintained to a large extent; this means a faster movement as compared to conventional systems. Thus, a determined and corporally displaced end position of the front teeth is achieved due to slight adaptive, undulating or tilting movements during the course of movements.

In conventional arrangements and methods, in particular according to FIG. 1, the point of rotation always remains in the center of the slot, so that the front teeth are moved through the bone like ploughs. In the arrangement according to FIG. 2, the point of rotation can even move down into the tips of the roots, depending on the thickness of the wire, and can lead to the fact that the crowns 8 are mainly tilted downwards in the distal direction, i.e. are extruded. In contrast thereto, the construction according to the present invention is a flexible system which causes a displacement of the point of rotation, depending on the past movement of an activation process from the bottom to the top and back, since against the sagital activation and against the extruding torque forces always a vertical moment is included in the loop 22, e.g. by a bend.

In order to increase the vertical and sagital component, the spring hook 22 is formed for simultaneously hooking in rubber bands 24, springs or ligatures. Thus, in addition to intrusion components, also lever moments with a minimum sagital force can be used. This embodiment of the appliance according to the present invention is shown in more detail in FIGS. 3, 5 and 13. Depending on the application, the rubber bands 24, springs or ligatures can be fixed at the same and/or opposite jaw. Preferably, the rubber bands 24, springs or ligatures are, on the one hand, fixed at the spring hook 22 and, on the other hand, at an end 26 of the arch 12 which projects from the tieback loop 20. Depending on the position of the anchoring end, more sagital forces or more vertical forces are caused.

By means of the appliance according to the present invention, preferably a so-called deep bite can be regulated, but also only an angulation and/or extrusion can be caused. In this connection, no undesired friction occurs, the vertical components are clearly supported and the original arch shape is stabilized. Moreover, only very slight anchoring problems occur; thus, very purposeful movements and above-average movement speeds of the teeth can be caused. This is particularly due to the fact that the appliance according to the present invention is an absolutely flexible and biologically oriented system.

Figure 5:
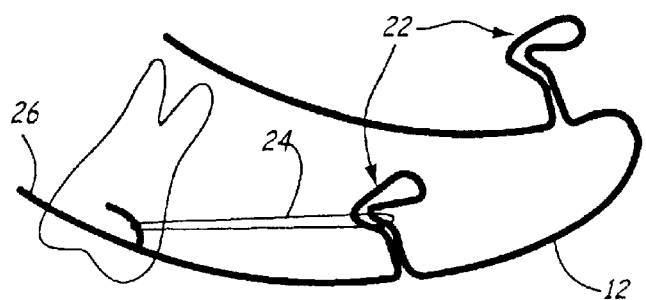
FIG. 5 is a further embodiment of the square arch according to the present invention with a rubber band, a spring and a ligature.

FIG. 6 shows a conventional straight, non-bent (non-broken) arch in the activated state in which a front torque and/or a strong angulation of the wire is/are bent in at the tooth No. 6. In the area 28 of the teeth Nos. 3, 4 and 5 there are conventionally strong vertical elastic bends, which are undesired. This elastic deformation can be counteracted by a bent-in bend in the arch, as shown in FIG. 5; then it could, however, be present more intensively in the area of the loop 22. This negative counter effect can be counteracted by stronger angulation bends at the spring hook and/or by hooking in a rubber band 24 or a ligature from the loop 22 to the teeth Nos. 6 or 7, wherein additionally a gap closure movement is integrated. In the prior art system shown in FIG. 1, this elastic or also plastic bend would in any case cause additionally considerable friction problems.

Figure 4:
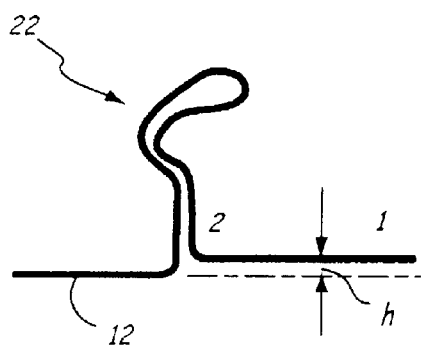
FIG. 4 is an embodiment of the square arch according to the present invention with opened spring.

In a different embodiment of the present invention as shown in FIG. 4, a height difference h between the legs of the arch 12 can be provided in order to locally include additionally vertical force components acting on the teeth.

The appliance according to the present invention can be used in a differentiated manner in all three dimensions and operated individually and flexibly, corresponds to the biological requirements as regards force, dimension and flexibility, causes a minimum anchorage loss (the rear anchorage teeth do not move or move only slightly in the mesial direction), and the above described disadvantages of conventional techniques are minimized or eliminated by means of the technique of the present invention.

The appliances according to the present invention can have different arch sizes, loop sizes, loop positions, loop inclinations and wire dimensions and consist of different materials. The arches described above can be produced with or without tieback loops or similar loops. For example, the tieback loop 20 can be replaced in that slightly in the distal direction of the last tooth, the arch is drawn through a bracket/band 10 attached thereto and bent. Thus, the contraction spring 22 could be activated as well.

The use of a tieback loop 20 is particularly advantageous in that due to a springing angulation the root of the tooth No. 7 can be held in the mesial direction in a manner being favorable as regards anchorage, and that due to the primary activation counter bends (vertical bends) can be provided in the arch 12 since no friction losses occur.

Due to the realization of the arch 12 in accordance with the present invention, in particular an intrusion of the front teeth (teeth Nos. 1, 2 and optionally 3) can be caused. For this purpose, the arch 12 can additionally be pre-bent in the area of the teeth Nos. 3, 4 and 5, so that during introduction into the slots of the brackets 10 and after a subsequent fixation therein, the arch 12 essentially extends in the sagital direction and thus causes an intrusion force component in the area of the teeth Nos. 1, 2 and (optionally) 3 due to the tension caused by the bend. This prebent wire of the arch 12 as shown in FIG. 5 can preferably be combined with the system which is shown in FIG. 4 and described above.

Figure 7:
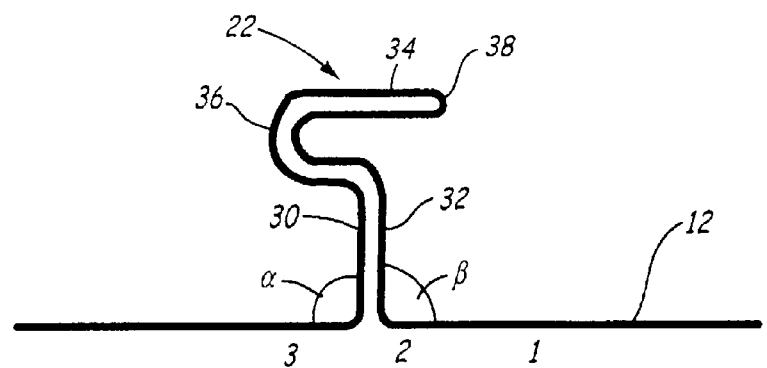
FIGS. 7–13 are further embodiments of the arch according to the present invention.
Figure 8:
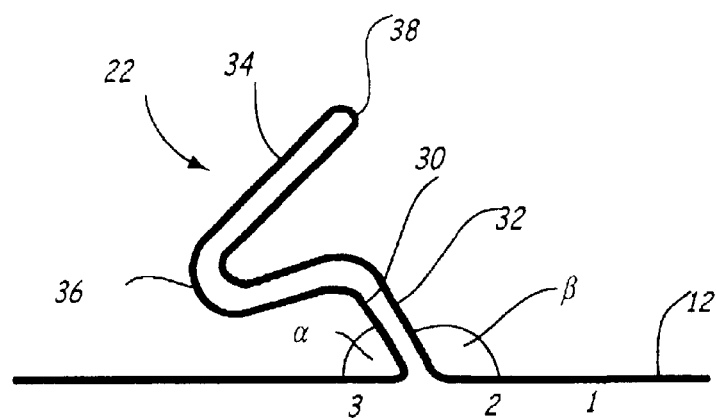

In FIGS. 7 to 17 different embodiments of the arch 12 according to the present invention are shown exemplarily. Depending on the application, the spring hook 22 is formed with individual inclination angles a for a first hook arm 30 and β for a second hook arm 32. With the same bend shape of the loop 22, the angle α decides about the load areas in the area of the front teeth since the vertical link is, as shown in FIG. 7, more in the vertical area of the tooth No. 2 and less in the area of the tooth No. 1. In FIG. 8 the link is more in the area of the teeth Nos. 2 and 1. Not only the inclination angle a but also the inclination angle p are decisive for more vertical counter forces against torque and tilting of the crowns of the teeth Nos. 1 and 2 in the distal direction. These inclination angles and the forces resulting therefrom can be adjusted individually, depending on the situation, by previously bending the wire, i.e. they can be "pre-bent".

Also the position of the angulation of an upper loop area 34 is different for vertical and sagital forces as well as for an easier hooking-in of rubber bands. For example, for a deep bite the embodiment shown in FIG. 8 is preferably more favorable. Bend areas 36 and 38 formed at the spring hook 22 as well as all other bends or arches should preferably be shaped continuously or bulgedly, in order to influence the sliding movement of the point of rotation uniformly.

Figure 9:
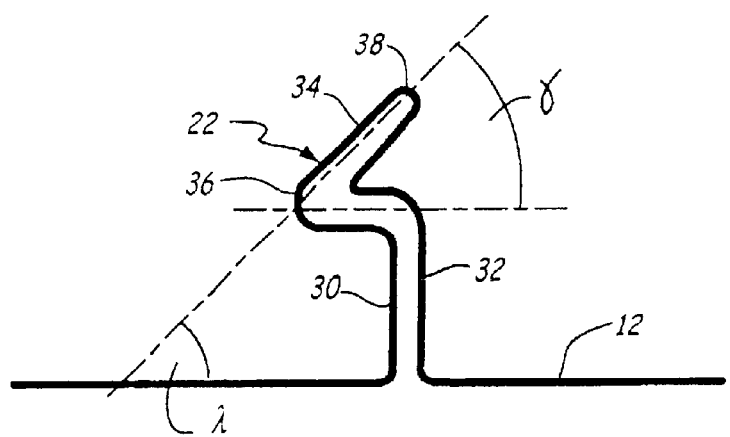

As already explained above, the dimensions of the angles α and β can be realized in different manners, wherein they can be equal or different. Moreover, the angle α can also be not equal 180°-β and vice versa. The opening angle γ of the spring hook 22 can, as shown in FIG. 9, vary between 0° and 180°, preferably 0° to 90° or 30° to 90°. Moreover, also the inclination angle λ of the upper loop area 34 can be variable. The angles γ and λ can moreover be different from each other. Preferably, the angles γ and λ lie in the range between 30° and 60°, more preferably between 40° and 50°, particularly preferably at about 45°.

Figure 10:
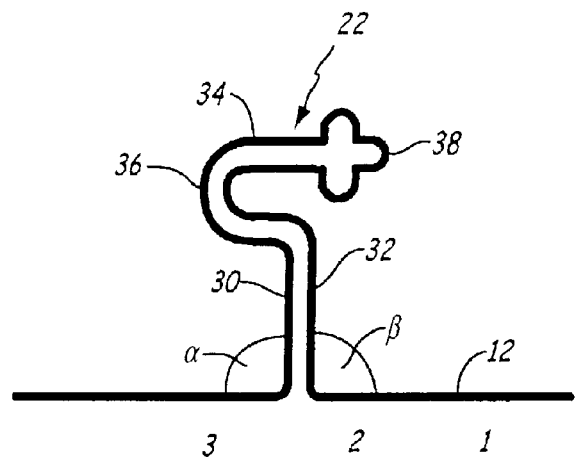
Figure 11:
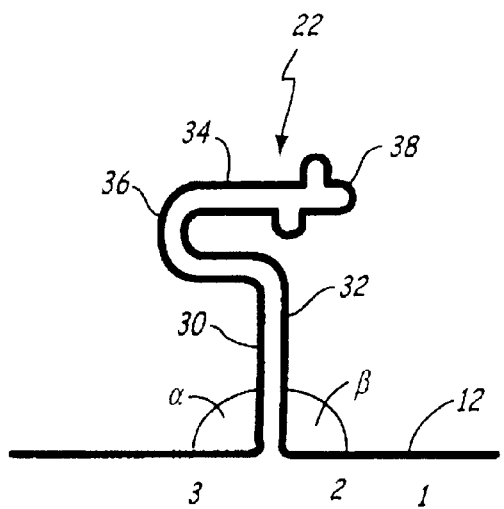
Figure 12:
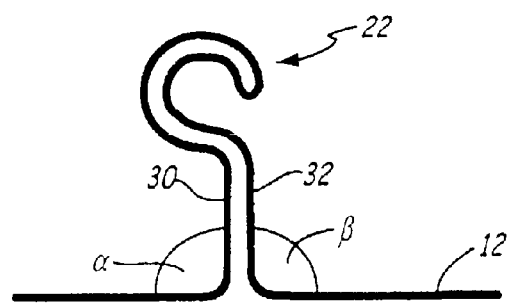
Figure 13:
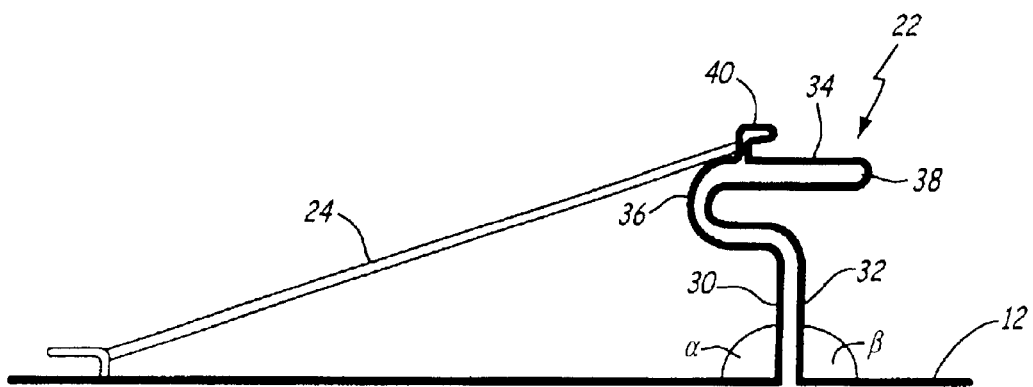

On the basis of the above description of the embodiments according to FIGS. 7 to 9 it is clear that a plurality of shapes and positions of the spring hook 22 can be provided for the arch 12 according to the present invention. For example, the bends can have a circular, elliptical and/or drop shape. Also edges and kinks can be provided. In addition to the hook shapes shown in FIGS. 7 to 9, the arch according to the present invention can have a plurality of further shapes. For example, the hook 22 can have further bends in the upper area 34 or in the area opposite thereto, as shown in FIGS. 10, 11 and 13. According to FIG. 13, it is in particular also possible to form a hook or a loop 40 in the bend provided in the area 34 in order to attach rubber bands 24 or the like thereto. FIG. 12 shows an alternative, very bulged hook shape which is bent at an angle of about 180°.

The dimensions of the spring hook 22 can vary depending on the application. In particular the height and the position of the individual portions of the spring hook 22 can be varied depending on the purpose, whereby different lever arms and thus forces and moments can be imparted to the teeth to be regulated. By a combination of the different angles and lengths of the spring hook 22, a plurality of shapes of the spring hook 22 are possible.

Figure 14:
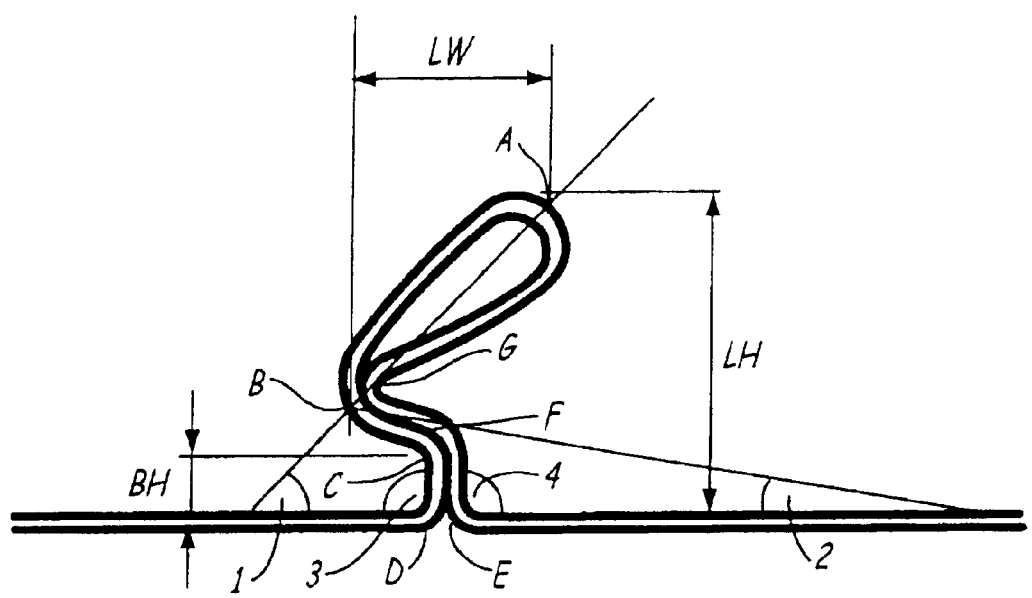
FIG. 14 is a preferred embodiment of the spring hook.

A particularly preferred embodiment of the arch of the present invention with the spring hook 22 is shown in FIGS. 14 to 17. With reference to FIG. 14, first the individual portions of the spring hook are defined. The distance between the two summits A and B is called the loop length LL. The distance between the points C and D defines the base height BH of the spring hook 22. The distance connecting points B and F is the base length BL. The total height of loop height LH of the spring hook 22 and the total width or loop width LW is also shown in FIG. 14. The summits A and B also define the loop axis. In the preferred embodiment of the arch according to the present invention as shown in FIGS. 14 to 17, the spring hook 22 is shaped such that the angle 1 has about 45°, wherein the angles 3 and 4 (or αand β) have 90°. The connection between the points B and F, which defines the base of the loop, is formed in this preferred embodiment with the angle 2 of about 10° to 20°. The points A to G are preferably the intersections of the respective bends.

The dimensions of FIGS. 15 to 17 are indicated in Inch. According to FIG. 14, the thickness of the wire of the arch is 0.016 Inch (0.41 mm). The height of the spring hook 22 measured from the upper edge of the wire is 0.280 Inch (7.11 mm). The total width LW of the spring hook 22 is 0.186 Inch (4.72 mm), wherein the head area of the spring hook 22 forming the loop with the summit A is spaced by 0.111 Inch (2.82 mm) from the space between the foot legs 30 or 32. The two foot legs 30 and 32 have a distance of 0.004 Inch (0.1 mm) from each other. The base, i.e. the line connecting the points B and F, is inclined by an angle of about 10° to 20° with respect to the horizontal line. The loop axis between the points A and B is inclined by an angle of about 45° so that between the base and the loop axis there is an angle of, e.g., about 65°. The radius in the area of the loop head, i.e. at the point A is about 0.035 Inch (0.89 mm). The remaining radiuses formed in the area of the loop have a radius of about 0.020 Inch (0.51 mm).

As shown in FIG. 16, the radius of the arch in the area of the front teeth is 1.0625 Inch (27 mm), wherein this circular bend is formed on both sides of the mesial or center line of the arch along an angle of 75°. Following both sides of the circular arch, respective essentially straight arch portions are provided which each open at an angle of about 15°, whereby a total width of the arch of 2.834 Inch (72 mm) with a total length of 3.016 Inch (76.6 mm) is formed.

The loop axis defined by the points A and B is essentially responsible for the elasticity of the system. Moreover, also the angle 2 is important for the elasticity of the loop during opening and closing, since depending on its dimensions more vertical or more transversal loads are directed to the point D or to distal parts. The smaller the angle 2 becomes, the larger is the vertical force component occurring in the area of the point C; this is synonymous with an elasticity reduction. The point G is essentially the center of the loop and is in the area between the points B and C; thus, mechanical forces are supported for intruding the front during sagital opening and closing movements. Also the point G is partially responsible for the elasticity of the loop. In the area of the point G there is essentially the stiffest point of the loop. Moreover, the point G is the starting point for a lever by means of which the front is moved. The height of the point G depends on length of the lever arm with regard to the front teeth. The closer this point is with respect to the resistance center of the front teeth or a point above it, the lighter force is required for a corporal intrusion and distalization of the front teeth. The lower the anchorage losses are, the better can the intrusion, the torque and the corporal displacements be controlled.

In the clinically non-activated state, the spring hooks 22 are closed at the bottom, i.e. at the hook foot or the transition to the straight bend, as shown in FIG. 7, and can then be pre-tensioned or activated.

However, the spring hooks 22 can also be opened slightly, as shown in FIGS. 8 and 9, so that the spring can be activated or tensioned individually due to an intensification of the loop shape at one of the plurality of desired positions, since a change in the loop shape of the spring hooks 22 at different positions causes different tensions. However, also the hook shape of spring hooks 22 which are closed at their bottom can be changed individually.

Such spring hooks 22 then have, for example, only one basic shape for the hook which can be further changed depending on the application.

The arch 12 according to the present invention provides better torque and intrusion possibilities and minimizes or eliminates friction problems and anchorage losses. The arch 12 is a loop construction being made preferably of a stainless steel and having a square cross-section. Different wire sizes can be used (0.011×0.020; 0.012×0.020; 0.013×0.020 Inch). The brackets 10 can, for example, have 0.016×0.020 Inch slots. Such slot sizes allow a very early use of a square wire with at the same time very good control possibilities of all dimensions. The arch 12 according to the present invention allows a very good handling, optimum consideration of all biological aspects, integrates functional concepts and leads to more individual results as compared to conventional arches. Different angulations or angles, variations in the direction of the force and the shape of the spring hook 22 lead to a plurality of different possibilities in medical use. The spring hooks 22 of the arch 12 according to the present invention are also very effective for bite opening and torque control. The patient can manage it easily and it is very well accepted by him/her. The arch 12 according to the present invention is also more favorable with respect to the duration of the treatment, the comfort, the biological efficiency and anchorage losses as compared to conventional rigid systems.

The present invention provides a novel orthodontic arch having considerable advantages. The loops known so far are either vertical or horizontal loops. By means of the arch with spring hooks according to the present invention, which comprises a defined loop axis (e.g. 45°), it is possible to combine the advantages of known loops and to avoid the respective disadvantages of conventional loops. Thus, strong extrusion results in the front teeth, which are caused by torque and retraction, can be counteracted in a controlled manner. While the bulloop has relatively good contraction components, in this loop the vertical intrusion moments are very rigid and do not have a spring component. The front teeth tilt with the crowns in the distal direction and extrude. In this connection, the depth of the slot must be used as a lever arm against the long roots in order to distalize and intrude the roots. The T-loop, like the bulloop, has good vertical spring components; however, due to this property it is not a typical retraction spring. Moreover, due to the torque acting on the front, the front itself is extruded very much since this is not prevented by the spring, and during retraction this extrusion is further supported. During activation and during closing of the T-loop, mainly non-controllable vertical moments are caused; this moves the roots back and forth and thus damages and shortens the tips of the roots (resorption). Depending on the position of the T-loop, the front teeth or the incisor teeth are extruded more considerably. Thus, the T-loop is a poorly controllable spring for effecting corporal retractions and intrusions of teeth. If rubber bands are hooked in known systems, they immediately move into the bracket area; this further supports the extrusion forces which should just be avoided.

These disadvantages are avoided in the arch according to the present invention with the spring hook with the definedly bent loop axis. Moreover, the loop in the arch according to the present invention has the further advantage that rubber bands or the like can be hooked in at about the height of the point of rotation of the front teeth. This possibility is not given in the known loops. By means of the arch according to the present invention, a reactive movement of the rear teeth in the mesial direction is counteracted effectively so that a very controlled movement in the area of the front teeth can be achieved both in the vertical direction and the sagital direction. In the entire system of the invention very minimum forces can be applied; in the known loops this is only possible if other disadvantages (e.g. bad control in the vertical direction) are accepted.

What is claimed is:

1. An orthodontic arch which can be introduced in brackets being attached to teeth and at least portions of which extend in the sagital direction, wherein said arch is formed of a wire which is essentially prebent to an U-shape in the sagital direction and which comprises at least one spring hook in at least one area in a direction differing from the direction of the arch, wherein said spring hook is shaped such that it forms a loop axis (AB) which extends at an angle in the range between 30° and 60° with respect to the sagital direction.

2. The arch according to claim 1, wherein at least one distal end of said arch a loop for anchoring said arch at an anchorage tooth is provided.

3. The arch according to claim 1, wherein the wire for anchoring the arch at an anchoring tooth is bent at least one end of said arch.

4. The arch according to claim 1, wherein said spring hook is shaped for hooking in a rubber band, springs or a ligature.

5. The arch according to claim 4, wherein said spring hook is shaped such that a second anchoring point of said rubber band, the spring or the ligature can be provided in the area of the distal end of said arch.

6. The arch according to claim 5, wherein said spring hook is shaped such that the second anchoring point of said rubber band, the spring or the ligature can be provided between the distal end and said spring hook.

7. The arch according to claim 5, wherein said spring hook is shaped such that the second anchoring point of said rubber band, the spring or ligature can be provided at the same and/or opposite part of the jaw.

8. The arch according to claim 1, wherein said spring hook is located in an area in the distal direction of the teeth Nos. 2 or 3 and in the mesial direction of the teeth Nos. 4 or 5, i.e. in an area of about 10% to 50% of half the length of said arch away from the mesial line or center of the arch.

9. The arch according to claim 1, wherein in at least one area along said arch a pre-bent bend is provided in a direction differing from the sagital direction or arch direction.

10. The arch according to claim 1, wherein said essentially U-shaped arch has height differences and/or a step in a direction extending essentially vertically with respect to the direction of the arch.

11. The arch according to claim 1, wherein said spring hook extends from said arch at a first inclination angle a with a first hook arm and at a second inclination angle β with a second hook arm.

12. The arch according to claim 11, wherein said first inclination angle a is essentially equal to said second inclination angle β.

13. The arch according to claim 11, wherein said first inclination angle α is not equal to a complementary angle of 180° minus said second inclination angle β or said second inclination angle β is not equal to a complementary angle of 180° minus said first inclination angle α.

14. The arch according to claim 11, wherein said first inclination angle α is equal to the complementary angle of 180° minus said second inclination angle β or said second inclination angle β is equal to the complementary angle of 180° minus said first inclination angle α.

15. The arch according to claim 1, wherein said spring hook has an opening angle γ in the range between 30° and 60°.

16. The arch according to claim 1, wherein an upper area of said spring hook is provided at an inclination angle λ relative to said arch.

17. The arch according to claim 16, wherein said inclination angle λ is equal or not equal to said opening angle γ.

18. The arch according to claim 17, wherein said inclination angle λ lies between 0° and 180°.

19. The arch according to claim 1, wherein said spring hook is closed in a non-activated state.

20. The arch according to claim 1, wherein said spring hook has a basic hook shape which can be further adapted individually.

21. The arch according to claim 1, wherein said spring hook comprises a plurality of portions which extend in different directions with respect to said arch.

22. The arch according to claim 1, wherein said spring hook comprises at least one portion which does not extend vertically with respect to said arch.

23. The arch according to claim 1, wherein partial areas of said spring hook are shaped as a pressure spring and/or tension spring.

24. The arch according to claim 1, wherein bends in said spring hook comprise portions having a circular, elliptical and/or drop shape.

25. The arch according to claim 1, wherein in an upper area of said spring hook at least one further bend is provided, said bend being shaped for hooking in a rubber band, springs or a ligature.

26. The arch according to claim 1, wherein the wire is a square wire.

27. The arch according to claim 1, wherein said spring hook has a basis (BF) which is formed at an angle in the range between 10° and 25° with respect to the sagital direction.

28. An orthodontic arch which can be introduced in brackets being attached to teeth and at least portions of which extend in the sagital direction, wherein said arch is formed of a wire which is essentially prebent to an U-shape in the sagital direction and which comprises at least one spring hook in at least one area in a direction differing from the direction of the arch, wherein said spring hook has a basis (BF) which is formed at an angle in the range of between 10° and 25° with respect to the sagital direction, and wherein said basis comprises a guide on which an adjacent part of the spring hook can move during opening and/or closing of the hook.

29. The arch according to claim 28 wherein said spring hook is shaped such that it forms a loop axis (AB) which extends at an angle in the range between 30° and 60° with respect to the sagital direction.

* * * * *

UNITED STATES PATENT AND TRADEMARK OFFICE
CERTIFICATE OF CORRECTION

PATENT NO. : 6,595,774 B1
DATED : July 22, 2003
INVENTOR(S) : Georg Risse

Page 1 of 1

It is certified that error appears in the above-identified patent and that said Letters Patent is hereby corrected as shown below:

Title page,
Item [57], ABSTRACT, delete entire ABSTRACT and insert

-- An orthodontic arch including at least one special loop in the form of a spring hook. Said spring hook makes it possible to effect intrusion and corporal retraction of the front teeth, especially in the upper jaw, in a faster, more gentle and better controlled manner in comparison with conventional arches and methods. By additionally attaching rubber bands, springs or ligatures, all disadvantages of conventional constructions can be eliminated or minimized by an adjustable lever action effect due to the fact that the inventive arch-spring construction enables dynamic undulating movement of the front teeth adapted to biological processes during an activation procedure as opposed to conventional rigid mechanisms. Especially medical or biological requirements and aspects are fulfilled by the inventive arch. The inventive arch enables faster movement and greatly reduces damage and pain. In addition, the costs are lowered considerable by reducing the numbers of arches and by saving time.--

Column 1,
Line 2, insert

-- The present application claims priority of International patent application Serial No. PCT/EP99/10285, filed 22 December 1999, and published in German, which claims priority to German application Serial No. 198 59 503.4, filed 22 December 1998, the contents of which are hereby incorporated by reference in their entirety.--.

Column 10,
Lines 60 and 64, delete "a" and insert -- α --.

Signed and Sealed this

Fifth Day of October, 2004

JON W. DUDAS
*Director of the United States Patent and Trademark Office*